United States Patent [19]

Rubinstein et al.

[11] Patent Number: 4,617,378

[45] Date of Patent: Oct. 14, 1986

[54] PURIFICATION OF BIOLOGICALLY ACTIVE HUMAN IMMUNE INTERFERON

[75] Inventors: Menachem Rubinstein, Givat Shmuel; Jossef Friedlander, Bat Yam; Dina Fischer, Ramat Gan, all of Israel

[73] Assignee: Yeda Research and Development Co., Ltd., Rehovot, Israel

[21] Appl. No.: 571,735

[22] Filed: Jan. 18, 1984

[30] Foreign Application Priority Data

Feb. 13, 1983 [IL] Israel ........................................ 67896

[51] Int. Cl.$^4$ ..................... C07K 15/26; C07K 3/28; A61K 45/02; C12P 21/00
[52] U.S. Cl. ..................................... 530/351; 424/85; 435/68
[58] Field of Search ....... 424/85; 260/112 R, 112 SR; 435/68, 172.3; 530/351

[56] References Cited

U.S. PATENT DOCUMENTS 4,168,261  9/1979  Edy ........................................ 424/85
4,440,675  4/1984  Braude ................................. 435/811
4,485,017  11/1984  Tan et al. ............................ 435/811

OTHER PUBLICATIONS

Yip, Y. et al., Proc. Natl. Acad. Sci., vol. 79, pp. 1820–1824, 1982.

Primary Examiner—Blondel Hazel
Attorney, Agent, or Firm—Iver P. Cooper

[57] ABSTRACT

There is provided a process for purification of human immune interferon (IFN-γ) to homogeneity without appreciable loss of biological activity by the use of chromatography on controlled-pore glass, ultrafiltration and high performance cation exchange chromatography, resulting in essentially pure human interferon subtypes 21K and 26K, and there are provided said purified interferons and pharmaceutical compositions containing same.

14 Claims, No Drawings

PURIFICATION OF BIOLOGICALLY ACTIVE HUMAN IMMUNE INTERFERON

BACKGROUND OF THE INVENTION

Among the various types of human interferon, immune interferon (IFN-γ) is the least characterized. This interferon is produced in lymphocytes upon stimulation with mitogens or specific antigens and it differs significantly in its structure and properties from the virus-induced α- and β-interferons.

Recently, Yip et al., have reported a method of human IFN-γ production based on the stimulation of lymphocytes by a combination of the phorbol ester 12-O-tetradecanoyl-phorbol-13 acetate (TPA) and phytohemagglutinin (PHA)(1). Later, Yip et al. were able to purify two subtypes of IFN-γ by a preparative NaDodSO$_4$/polyacrylamide gel electrophoresis. However, an almost complete loss of biological activity had occurred during this step (2,3). These subtypes had an apparent molecular mass of 20,000 and 25,000, they corresponded to Coomassie blue-stainable protein bands, and were antigenically cross-reactive. A third minor component having an apparent molecular mass of about 43,000 daltons was also detected.

In another study, Gray et al. have reported the cloning and expression of human IFN-γ complementary DNA. The nucleotide sequence indicated that this IFN-γ was composed of a single polypeptide with 146 amino acids and a calculated molecular mass of 17,000 daltons. Furthermore, analysis of a gene library did not reveal any other structurally related DNA sequences (4). This data suggested that there is only one polypeptide sequence related to IFN-γ and that native IFN-γ may be partly dimeric.

Pestka and Rubinstein have previously described in U.S. Pat. No. 4,289,690 the purification to homogeneity of IFN-α and the separation of eight distinct subtypes by reverse phase high performance liquid chromatography (HPLC)(5,6,7). This method is not suitable for the purification of IFN-γ because IFN-γ is labile to organic solvents and low pH. The recent availability of ion exchange HPLC columns suitable for fractionation of proteins has allowed high resolution chromatography of IFN-γ preparations.

Recent scientific papers directed to the production, purification and structural studies of IFN-γ can be summarized as follows:

(1) Yip, Y. K., Pang. R. H. L., Urban, C. and Vilcek, J. (1981). Proc.Natl.Acad.Sci. USA 78, 1601–1605.
(2) Yip, Y. K., Barrowclough, B. S., Urban, C. and Vilcek, J. (1982). Science 215, 411–413.
(3) Yip, Y. K., Barrowclough, B. S., Urban, C. and Vilcek, J. (1982). Proc.Natl.Acad.Sci. USA 79, 1820–1824.
(4) Gray, P. W., Leung, D. W., Pennica, D., Yelverton, E., Najarian, R., Simonsen, C. C., Derynck, R., Sherwood, P. J., Wallace, D. M., Berger, S. L., Levinson, A. D. and Goeddel, D. V. (1982). Nature 295, 503–508.
(5) Rubinstein, M., Rubinstein, S., Familletti, P. C., Miller, R. S., Waldman, A. A. and Pestka, S. (1979). Proc.Natl.Acad.Sci. USA 76, 640–644.
(6) Rubinstein, M. (1979). Anal. Biochem. 97, 1–7.
(7) Rubinstein, M., Levy, W. P., Moschera, J. A., Lai-C. Y., Hershberg, R. D., Bartlett, R. and Pestka, S. (1981) Arch.Biochem.Biophys. 210, 307–318.

While several of the above papers contain claims to have purified human immune interferons to homogeneity, an almost complete loss (80–90%) of biological activity was admitted. Furthermore, none of the properties of the allegedly pure compounds were described.

The use of high performance liquid chromatography for purification of proteins is generally known in the art.

DESCRIPTION OF THE INVENTION

The present invention relates to an improved process for purifying human immune interferons and to the novel homogenous human immune interferons (IFN-γ) produced thereby.

The improved process of the present invention involves a combination of chromatography on controlled-pore glass, ultrafiltration and cation exchange high performance liquid chromatography steps to achieve efficient purification of IFN-γ.

It has been known in the art to employ chromatography on controlled-pore glass as a procedural step in the purification of IFN-γ (see ref. 2, 3). Ultrafiltration was broadly used in the past for concentration and desalting of proteins. In some cases, ultrafiltration could be used to remove peptides and proteins having a molecular weight lower than the cut-off value of the ultrafiltration membrane. Mono-S cation exchange HPLC columns were designed and marketed by Pharmacia Fine Chemicals specifically for the fractionation of proteins. However, the prior art did not utilize or suggest the use of these HPLC columns in conjunction with controlled pore glass chromatography and ultrafiltration for the fractionation of IFN-γ.

Since an international standard of IFN-γ does not exist yet, the biological activity given here and elsewhere in this invention is calibrated against interferon-α reference standard G-023-901-527 supplied by the National Institutes of Health (Bethesda, Md., U.S.A.) and utilizes human WISH cells (American Type Culture Collection Cat. No. CCL-23) and vesicular stomatitis virus in an assay based on the inhibition of the viral cytopathic effect. It is generally known in the art that the use of other cell lines, other viruses, and other standards may give a very wide range of specific activities. An additional variable is the protein content which may be determined by various procedures. The protein content in the present invention was based on an amino acid analysis which is widely accepted as an absolute method.

The use of controlled-pore glass chromatography on crude IFN-γ preparations results in about a 4-fold purification. Thus, IFN-γ produced by this step has a specific activity of about $2 \times 10^5$ units/mg. For controlled-pore glass (CPG) procedure the following protocol can be employed.

CPG beads were added to culture supernatants containing IFN-γ (3,000–16,000 units/ml), $8$–$20 \times 10^4$ units/mg) at a ratio of 1:100 (vol/vol) in a polypropylene centrifuge bottle. The mixture was stirred for 3 hrs at 4° C., the beads were allowed to settle, the supernatant was aspirated and the beads were packed into a siliconized glass column. The column was first washed with several column volumes of phosphate-buffered saline, and IFN-γ was eluted by 0.5M tetramethylammonium chloride pH 7.

The resulting purified interferon obtained by elution from CPG with tetramethylammonium chloride exhibits a specific activity of about $2 \times 10^5$ units/mg with a recovery of about 50–100%. Fractions containing IFN-γ activity from the CPG-chromatography were combined and salt was removed by ultrafiltration on a PM-10 membrane (Amicon). The retained fraction was washed with several volumes of 2 mM sodium phosphate (pH 7.4) and concentrated to about 0.5% of the original culture volume. Insoluble proteins were removed by centrifugation and the clear supernatant was stored at +4° C. until used. The resulting interferon concentrate obtained by ultrafiltration exhibits a specific activity of $9 \times 10^5$ units/mg with a recovery of about 60–100%.

In order to achieve further purification of the interferon concentrate produced by ultrafiltration, the interferon is processed through one or two cation exchange high pressure liquid chromatography (HPLC) steps with high resolution. The liquid chromatography step utilizes columns containing a monodisperse organic polymeric matrix to which sulfoalkyl groups are bonded. These columns, which can be used sequentially and under varying conditions of pH gradient and ionic strength gradients and in the presence of various stabilizers such as ethylene-glycol can purify human immune interferon to homogeneity as determined by obtaining a single band on sodium-dodecyl sulfate (SDS) polyacrylamide gel electrophoresis, a constant specific activity and a single peak on HPLC with activity and protein levels superimposeable.

The organic matrix cation-exchange HPLC columns used in the practice of the invention are articles of commerce. A suitable column is the Mono-S produced and marketed by Pharmacia Fine Chemicals, Uppsala, Sweden. A high pressure liquid chromatography system, for utilizing the aforesaid column, is available from a large number of manufacturers such as Pharmacia, Varian, Beckman, Waters Perkin Elmars, etc.

A preferred buffer system for eluting interferon-γ from the HPLC column in the present invention is 10 mM sodium phosphate pH 7.0, 20% vol/vol ethylene glycol. The procedure is carried out under a moderate pressure from about 10 to about 1000 PSI. The flow rate used for a standard $5 \times 50$ mm column is from 0.1 to 1.0 ml/min and the procedure can be performed at a range of temperatures from $-10°$ C. to $+30°$ C. Interferon-γ (from 0.1 mg to 10 mg protein) is adsorbed to the column and is then subsequently eluted in selective fashion using a gradient of increasing salt concentration. Suitable salts for this purpose include NaCl, KCl, $MgCl_2$, $MgSO_4$, tetramethylammonium chloride, and the like. Separation can be obtained in any pH value of a range varying from about pH 5 to about pH 8.5. In an alternative method the salt concentration remains constant and the pH is varied in an inceasing gradient from pH 5 to pH 10. Further purification can be obtained by performing two or more consecutive fractionations on the same column at either the same conditions or at different conditions as outlined above.

Fractionation of the eluate is accomplished by utilizing fraction collectors in a manner known per se with concomitant monitoring of the protein content during fractionation by a protein monitor such as an ultraviolet detector operating at any wavelength in the range of 210–280 nm and preferably at either 210 or 280 nm.

Due to the possible loss of IFN-γ by adsorption to silica and to glass, all tubings, containers and test-tubes under in the present invention were made of either teflon, polypropylene or polyethylene.

The highly purified preparations were most stable when stored at +4° C. in polypropylene test tubes and in the presence of 20% vol/vol ethylene glycol. Significant loss of biological activity was noticed in repeated freezing-thawing cycles.

Four major peaks of biological activity eluting at NaCl concentrations of 0.15, 0.20, 0.25 and 0.26 molar (at pH 7.0) were obtained with an overall recovery of 20–40%. Since the separation was performed under non denaturing conditions each peak represented a discrete sub-type of HuIFN-γ. Analysis by $NaDodSO_4$-polyacrylamide gel electrophoresis either in the presence or in the absence of β-mercaptoethanol revealed that the peaks eluting at 0.25M and 0.26M NaCl contained single protein bands with apparent molecular masses of 26,000 (26K), and 21,000 (21K) respectively, while the peaks at 0.15M and 0.20M were less pure. The specific activity of both subtypes 26K and 21K was $7 \times 10^6$ units/mg. Analysis by gel filtration on a Ultrogel AcA54 column of either crude or any of the purified IFN-γ subtypes under non denaturing conditions gave a peak of biological activity corresponding to a molecular mass of 45,000 daltons. Amino acid analysis of subtypes 26K and 21K showed a general similarity to the theoretical values calculated from the sequence of the cDNA clone as described by Gray et al. (4). However, significant differences in the levels of proline, glycine and panylalanine were observed Subtypes 26K and 21K gave almost identical amino acid compositions and peptide maps.

Interferon-γ have exhibited antiviral activity, anti cellular activity, ability to augment natural and antibody dependent killer cell activity, monocyte and macrophage activation properties and ability to induce certain HLA surface marker antigens. These activities have been obtained with relatively crude preparations containing a large number of biologically active lymphokines. The purified homogenous human immune interferons of the present invention can be utilized in order to identify those activities belonging to IFN-γ proper. Preparations containing the purified IFN-γ can be used for clinical studies to estimate their usefulness in a variety of viral and neoplastic diseases.

The process and product aspects of this invention are further illustrated by reference to the following examples:

EXAMPLE 1

Production of Human IFN-γ.

Mononuclear cells were isolated from buffy coats by centrifugation ($400 \times g$, 30 min) on a Ficoll-Hypaque gradient. IFN-γ was induced in cultures of mononuclear cells ($5 \times 10^6$/ml) in serum-free RPMI-1640 medium by addition of 12-O-tetradecanoyl phorbol-13-acetate (5 ng/ml) and purified phytohemagglutinin (5 μg/ml). After 24 hrs of incubation at 37° C. and a 5% $CO_2$ atmosphere, cells were removed by centrifugation, culture supernatants were collected and stored at +4° C.

EXAMPLE 2

Chromatography on controlled-pore glass and ultrafiltration.

CPG beads were added to culture supernatants containing IFN-γ (3,000–16,000 units/ml), $8–20 \times 10^4$ units/mg) at a ratio of 1:100 (vol/vol) in a polypropylene centrifuge bottle. The mixture was stirred for 3 hrs at 4° C., the beads were allowed to settle, the supernatant was aspirated and the beads were packed into a siliconized glass column. The column was first washed with several column volumes of phosphate-buffered saline, and IFN-γ was eluted by 0.5M tetramethylammonium chloride pH 7. Fractions containing IFN-γ activity from the CPG-chromatography were combined and salt was removed by ultrafiltration on a PM-10 membrane (Amicon). The retained fraction was washed with several volumes of 2 mM sodium phosphate (pH 7.4) and concentrated to about 0.5% of the original culture volume. Insoluble proteins were removed by centrifugation and the clear supernatant was stored at +4° C. until used.

EXAMPLE 3

High Performance Liquid Chromatography (HPLC).

HPLC was performed on an Altex Model 330 liquid chromatograph (Beckman Instruments). A Mono-S HPLC cation-exchange column (5×50 mm) was equilibrated with 10 mM sodium phosphate pH 7.0-20% (vol/vol) ethylene glycol (Buffer A). IFN-γ preparation from the previous step was loaded at a flow rate of 0.5 ml/min. The column was then washed with Buffer A for 30 min followed by a 60 min linear gradient of NaCl (0-400 mM) in Buffer A. Each fraction (1 ml) was then assayed for IFN-γ activity and for protein content using bovine serum albumin as a protein standard. High resolution was achieved only when ethylene glycol was included in the elution buffers. Several peaks of biological activity eluting at NaCl concentrations of 0.15M, 0.20M, 0.25M and 0.26M were consistently obtained. Usually the peak at 0.25M was the most predominant. The peaks of biological activity at 0.25M and 0.26M were associated with two distinct protein peaks and their specific activity in various preparations was $7 \times 10^6$ units/mg. The peaks of biological activity at lower NaCl concentrations (0.15M and 0.20M) had lower specific activities and could not be associated with discrete protein peaks. The total recovery of biological activity was 20-40% with losses mainly at the last step.

EXAMPLE 4

NaDodSO₄-polyacrylamide Gel Electrophoresis and amino acid analysis.

Protein samples were first dialyzed against 2 mM sodium phosphate pH 7.4, dried in a Speedvac Concentrator (Savant), dissolved in a freshly prepared sample buffer with 2% β-mercaptoethanol and heated for 5 min at 100° C. A slab gel of 15% polyacrylamide was used. After electrophoresis, protein bands were visualized either with Coomassie blue or by silver stain. The fraction eluting at 0.26M salt gave a single protein band with an apparent molecular mass of 21,000 daltons (subtype 21K). The fraction eluting at 0.25M salt gave a major protein band with an apparent molecular mass of 26,000 (subtype 26K), but some minor bands of very low molecular masses were occasionally seen. Rechromatography of this fraction on the same HPLC column had eliminated these contaminants. The peaks of biological activity eluting at lower salt concentrations (0.15-0.20M) exhibited several major protein bands including a band corresponding to Mr 26,000. The apparent molecular masses of peaks 21K and 26K were not affected by treatment with β-mercaptoethanol prior to gel electrophoresis.
Amino acid Analysis.

Acetone (4-5 volumes) was added to samples containing IFN-γ (10-30 μg) from the Mono-S column. The mixtures were left 3-16 hrs at −20° C., spun (13,000×g, 5 min) and the precipitate was dried in a vacuum. Amino acid analysis was performed on a Durrum 500 analyser after hydrolysis (6N HCl, 110° C., 24 h). No correction for Serine or Threonine was made. Amino acid analysis of both subtypes 21K and 26K gave values quite similar to those calculated from the sequence of the gene. The high content of glycine was probably due to contaminants and to destruction of other amino acids during hydrolysis.

| Amino Acid Compositions of IFN-γ | | |
| --- | --- | --- |
| Amino Acid | Subtype 21K | Subtype 26K |
| Asx | 14.6 ± 1.3 | 16.5 ± 0.4 |
| Thr | 7.9 ± 0.4 | 7.4 ± 0.6 |
| Ser | 9.1 ± 1.4 | 10.8 ± 1.0 |
| Glx | 15.6 ± 0.7 | 16.4 ± 1.4 |
| Pro | 9.7 ± 1.4 | 8.0 ± 0.4 |
| Gly | 14.4 ± 0.3 | 14.3 ± 1.9 |
| Ala | 12.0 ± 1.5 | 11.3 ± 0.7 |
| Cys | 0.6 ± 0.5 | 0.6 ± 0.4 |
| Val | 7.4 ± 0.7 | 8.9 ± 0.9 |
| Met | 2.3 ± 1.0 | 0.8 ± 0.3 |
| Ile | 5.0 ± 0.3 | 6.0 ± 0.3 |
| Leu | 9.2 ± 0.3 | 12.9 ± 0.1 |
| Tyr | 2.9 ± 0.4 | 2.1 ± 0.1 |
| Phe | 4.9 ± 1.0 | 5.2 ± 0.8 |
| His | 3.5 ± 0.7 | 2.2 ± 0.3 |
| Lys | 20.3 ± 0.4 | 13.6 ± 3.1 |
| Arg | 5.7 ± 0.4 | 8.4 ± 1.0 |

EXAMPLE 5

Parental Dosage Form with Homogenous Human Immune Interferon Subtype 26K.

A total of 10 mg of homogenous human immune interferon subtype 26K having a specific activity of $7 \times 10^6$ units/mg is dissolved in 35 ml of normal serum albumin (human) USP. The solution is dialyzed against phosphate buffer saline with several changes to eliminate low molecular weight contaminants and then passed through a bacteriological filter. The filtered solution is aseptically subdivided into 140 vials. Each vial contains $5 \times 10^5$ units of the pure interferon suitable for parental administration. The vials are preferably stored in the cold (−20° to −70° C.) prior to use.

EXAMPLE 6

Parental Dosage Form with Homogenous Human Immune Interferon Subtype 21K.

A total of 10 mg of homogenous human immune interferon subtype 21K having a specific activity of $7 \times 10^6$ units/mg is dissolved in 35 ml of normal serum albumin (human) USP. The solution is dialyzed against phosphate buffer saline with several changes to eliminate low molecular weight contaminants and then passed through a bacteriological filter. The filtered solution is aseptically subdivided into 140 vials. Each vial contains $5 \times 10^5$ units of the pure interferon suitable for parental administration. The vials are preferably stored in the cold (−20° C. to −70° C.) prior to use.

EXAMPLE 7

Parental Dosage Form with Homogenous Human Immune Interferon Subtype 26K and 21K.

A combination of 5 mg of homogenous human immune interferon subtype 21K and 5 mg of homogenous human immune interferon subtype 26K, both having a specific activity of $7 \times 10^6$ units/mg is dissolved in 35 ml of normal serum albumin (human) USP. The solution is dialyzed against phosphate buffer saline with several changes to eliminate low molecular weight contaminants and then passed through a bacteriolgical filter. The filtered solution is aseptically subdivided into 140 vials. Each vial contains $5 \times 10^5$ units of the pure interferon suitable for parental administration. The vials are preferably stored in the cold ($-20°$ C. to $-70°$ C.) prior to use.

We claim:

1. A process for isolating a biologically active human interferon gamma protein species, without contamination or inactivation by sodium dodecyl sulfate, said species being selected from the group consisting of the 21k and 26k subtypes, which comprises in combination:
   (a) contacting impure interferon gamma containing at least one of said subtypes with a controlled pore glass absorbent, and eluting said interferon, obtaining said interferon in selected fractions as an eluate of enhances purity;
   (b) concentrating the eluate of step (a) by ultrafiltration on a membrane, the fraction retained on said membrane being interferon of further enhanced purity; and
   (c) passing the retained fractions of step (b) at least once through a cation-exchange matrix, and eluting at least one fraction containing said human biologically active interferon gamma protein species essentially free of non-interferon proteins, and also essentially free of other species of human interferon gamma.

2. The process of claim 1 wherein subtypes 26k is eluted in at least one fraction of step (c), and said fractions are pooled and rechromatographed on a cation exchange matrix so as to yield subtype 26k essentially free of subtype 21k.

3. The process of claim 1 wherein subtype 21k is eluted in at least one fraction of step (c), and said fractions are pooled and rechromatographed on a cation exchange matrix so as to yield subtype 21k essentially free of subtype 26k.

4. The process of claim 1 in which step (c) is carried out under HPLC conditions.

5. The process of claim 1 in which the cation exchange matrix comprises an organic polymer bearing sulfoalkyl groups.

6. The process of claim 5 in which the matrix is a Mono-S cation exchange column.

7. The process of claim 1 in which in at least one step (c) fraction, subtype 21k is eluted essentially free of subtype 26k, and in at least one other step (c) fraction, subtype 26k is eluted essentially free of subtype 21k, whereby subtypes 21k and 26k are coproduced in essentially homogeneous form.

8. The process of claim 1 in which the interferon is eluted in step (c) by increasing salt concentration.

9. The process of claim 1 in which the interferon is eluted in step (c) by increasing pH.

10. The process of claim 1 in which the interferon is eluted in step (c) in the presence of an interferon stabilizer.

11. The process of claim 1 in which the membrane of step (b) has a molecular weight cutoff of about 10,000 daltons.

12. The process of claim 1, wherein said species is purified to a specific activity of at least $7 \times 10^6$ U/mg.

13. The process of claim 12, wherein subtype 26k is eluted in step (c) by increasing salt concentration and collecting the fraction eluted at 0.25M salt concentration.

14. The process of claim 12, wherein subtype 21k is eluted in step (c) by increasing salt concentration and collecting the fraction eluted at 0.26M salt concentration.

* * * * *